(12) United States Patent
Pursley

(10) Patent No.: US 10,631,970 B1
(45) Date of Patent: Apr. 28, 2020

(54) REMOVAL ASSIST CATHETER FOR ENGAGING IVC FILTER STRUT INDEPENDENT OF STRUT ORIENTATION

(71) Applicant: Matt D. Pursley, Dawsonville, GA (US)

(72) Inventor: Matt D. Pursley, Dawsonville, GA (US)

( * ) Notice: Subject to any disclaimer, the term of this patent is extended or adjusted under 35 U.S.C. 154(b) by 136 days.

(21) Appl. No.: 15/480,267

(22) Filed: Apr. 5, 2017

Related U.S. Application Data

(60) Provisional application No. 62/318,721, filed on Apr. 5, 2016.

(51) Int. Cl.
| | | |
|---|---|---|
| *A61F 2/01* | (2006.01) | |
| *A61M 25/01* | (2006.01) | |
| *A61M 25/00* | (2006.01) | |

(52) U.S. Cl.
CPC .......... *A61F 2/01* (2013.01); *A61F 2/013* (2013.01); *A61M 25/0147* (2013.01); *A61F 2002/011* (2013.01); *A61M 2025/0079* (2013.01); *A61M 2025/0096* (2013.01)

(58) Field of Classification Search
CPC ...... A61F 2/013; A61F 2/01; A61F 2002/011; A61B 2017/320716; A61B 17/32056; A61B 17/221; A61B 2017/2217; A61B 17/3205; A61B 17/32053; A61B 17/22; A61M 2025/018
See application file for complete search history.

(56) References Cited

U.S. PATENT DOCUMENTS

| | | | | | |
|---|---|---|---|---|---|
| 5,893,369 | A | * | 4/1999 | LeMole | A61B 17/11 606/184 |
| 7,651,503 | B1 | * | 1/2010 | Coe | A61B 17/320016 606/108 |
| 2004/0138685 | A1 | * | 7/2004 | Clague | A61B 17/12 606/167 |
| 2005/0222598 | A1 | * | 10/2005 | Ho | A61B 17/32 606/171 |
| 2014/0180267 | A1 | * | 6/2014 | Vetter | A61B 10/0266 606/33 |
| 2016/0374717 | A1 | * | 12/2016 | Steele | A61B 17/320758 606/159 |

\* cited by examiner

*Primary Examiner* — Katrina M Stransky
(74) *Attorney, Agent, or Firm* — Jeffrey L. Thompson; Thompson & Thompson, P.A.

(57) ABSTRACT

A device for assisting in the removal of items endovascularly includes a catheter, an engagement head, and a pull rod. The pull rod has a proximal portion and a distal end connected to the engagement head. The pull rod is movable within the catheter to selectively extend and retract the engagement head from the distal end of the catheter. The engagement head is arranged to grab an item without regard to a particular orientation of the item. The engagement head has a generally cylindrical outer shape that corresponds to an internal surface of the catheter. The engagement head has a serrated proximal edge arranged to grab and hold an item against the distal end of the catheter, and an internal relief area located radially inwardly from said serrated proximal edge to aid in engaging an item.

12 Claims, 4 Drawing Sheets

REMOVAL ASSIST CATHETER FOR ENGAGING IVC FILTER STRUT INDEPENDENT OF STRUT ORIENTATION

RELATED APPLICATIONS

This application claims the benefit of Applicant's provisional U.S. Patent Application No. 62/318,721 filed on Apr. 5, 2016. This application is also related to Applicant's U.S. patent application Ser. No. 14/214,344 filed on Mar. 14, 2014 (now U.S. Pat. No. 9,301,828), and U.S. patent application Ser. No. 14/214,273 filed on Mar. 14, 2014 (now U.S. Pat. No. 9,592,079). The entire contents of these related applications are incorporated herein by reference.

BACKGROUND OF THE INVENTION

Field of the Invention

The present invention relates generally to catheters, and in particular to catheters that can be used to assist in removal of items endovascularly.

Description of the Related Art

Inferior vena cava filters ("IVC filters") are medical devices that can be implanted into the inferior vena cava to prevent pulmonary emboli (PE). IVC filters are sometimes recommended for patients with contraindications to anticoagulation who either have acute PE or acute proximal (above the knee) deep vein thrombosis. IVC filters are normally placed by compressing them into a thin catheter, and inserting them via a blood vessel, such as the femoral vein, the internal jugular vein, or the arm veins. Once the distal end of the catheter reaches the IVC, the IVC filter is pushed through the catheter and deployed into the desired location.

IVC filters are typically attached to the vena cava by hooks on their ends. Some IVC filters are compression springs, which compress outward onto the sidewall of the vena cava; however, they still have small hooks that retain their location. These hooks aid in the anchoring and healing process, but they make it difficult to retrieve the IVC filter from the vena cava.

FIG. 1 shows an IVC filter 1 deployed in the inferior vena cava. IVC filters 1 are generally anchored by anchors 4 to prevent them from migrating. IVC filters 1 are removed by using a snare 2 and a retrieval sheath 3. Coupling the snare with the IVC filter 1 is difficult. The IVC filter 1 may not be vertically aligned making it difficult to snare. Body movement due to respiration and blood flow also make snaring the IVC filter 1 difficult.

As can be seen in FIG. 1, the snare 2 is attached to the top of the filter 1. As shown in FIG. 2, the sheath 3 is pushed down over the filter 1, capturing the filter 1 and its contents and removing the filter anchors 4 from the vein wall. This allows the filter 1 to be removed. However, on occasion the filter anchors 4 or a portion of the filter 1 become embedded to the vein wall, and this removal procedure cannot be performed.

There is a need for an improved tool to assist with the removal of IVC filters after they have been deployed and to perform other endovascular operations.

SUMMARY OF THE INVENTION

The present invention provides a device for assisting in the removal of items endovascularly. The device includes a catheter, an engagement head, and a pull rod. The pull rod has a proximal portion and a distal end connected to the engagement head. The pull rod is movable within the catheter to selectively extend and retract the engagement head from the distal end of the catheter. The engagement head is arranged to grab an item without regard to a particular orientation of the item or the rotated position of the catheter. The engagement head has a generally cylindrical outer shape that corresponds to an internal surface of the catheter. The engagement head has a serrated proximal edge arranged to grab and hold an item against the distal end of the catheter, and an internal relief area located radially inwardly from the serrated proximal edge to aid in engaging an item.

According to one aspect of the invention, a device for assisting in the removal of items endovascularly is provided, comprising: a catheter having a proximal end and a distal end; an engagement head arranged to be extended from and retracted into the catheter; and a pull rod having a proximal portion and a distal end connected to the engagement head. The pull rod is movable within the catheter to selectively extend and retract the engagement head from the distal end of the catheter.

According to another aspect of the invention, a device for assisting in the removal of items endovascularly is provided, comprising: a catheter having a proximal end and a distal end; and an engagement head that can be extended from and retracted into the catheter. The engagement head comprises a cylindrical outer shape that corresponds to an internal surface of the catheter, and a proximal edge that is generally circular and faces in a proximal direction. The engagement head is arranged to grab and hold an item between the proximal edge and the distal end of the catheter. A pull rod having a proximal portion and a distal end is connected to the engagement head. The distal end of the pull rod is spaced radially inwardly from the proximal edge, and the pull rod is movable within the catheter to selectively extend and retract the engagement head from the distal end of the catheter.

Numerous other objects of the present invention will be apparent to those skilled in this art from the following description wherein there is shown and described an embodiment of the present invention, simply by way of illustration of one of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the invention is made with reference to the accompanying drawings. In the drawings.

DETAILED DESCRIPTION OF THE INVENTION

Figure 1:
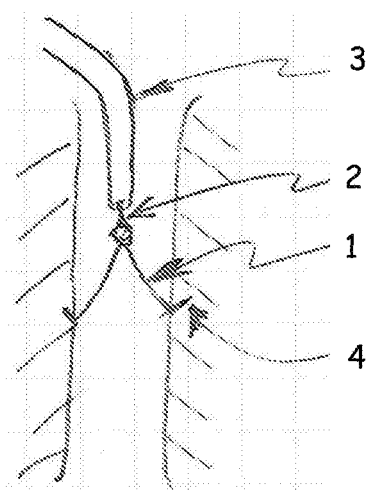
FIG. 1 illustrates a conventional retrieval sheath for removing an IVC filter deployed in the inferior vena cava.
Figure 2:
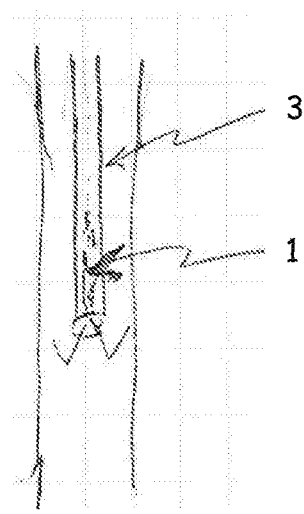
FIG. 2 illustrates the process of using the conventional retrieval sheath shown in FIG. 1.

A device 10 for assisting removal of items endovascularly will be described in detail with reference to FIGS. 3 to 7 of the accompanying drawings.

The device 10 of the present invention can be used to assist in removal of items endovascularly, such as an IVC filter or filter strut 11. As shown in FIGS. 3 to 7, the device 10 includes a catheter 12, an engagement head 13, and a pull rod 14. The catheter 12 has a proximal end 15 and a distal end 16. The engagement head 13 is arranged to be extended from and retracted into the distal end 16 of the catheter 12.

The device 10 is intended to give a physician the ability to enter a cavity, such as a vein, and make contact with and hold or pull an item, such as an IVC filter or an IVC filter strut 11. The device 10 can engage the IVC filter strut 11 independent of the orientation of the strut 11 and the catheter 12. The device 10 can be used to grab a portion of the IVC filter and free it from the vein wall.

The device 10 can be used in combination with an IVC filter retrieval device having a side port, as described in Applicant's related U.S. Pat. Nos. 9,301,828 and 9,592,079. The device 10 can be used in place of the catheter with a C-shaped cutting head described in the related '828 and '079 patents. The C-shaped cutting head required a particular orientation of the C shape so that it would allow engagement of the IVC filter strut. In contrast, the engagement head 13 of the present invention does not require a particular orientation for operation.

Figure 7:
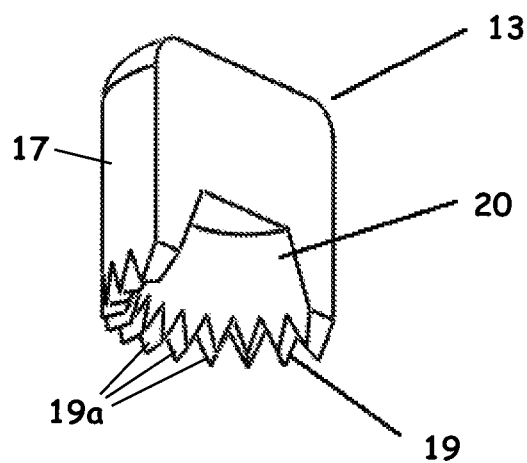
FIG. 7 is a perspective cutaway view of the engagement head of the removal assist device.

The engagement head 13 is shown in detail in FIG. 7. The engagement head 13 has a generally cylindrical outer shape 17 that corresponds in shape and size to an internal surface 18 of the catheter. A serrated proximal edge 19 is provided on a proximal side of the engagement head 13 and is arranged to grab and hold an item between the serrated proximal edge 19 and the distal end 16 of the catheter 12. The serrated proximal edge 19 is generally circular with a plurality of teeth 19a protruding in the proximal direction. The engagement head 13 has an internal relief area 20 located radially inwardly from the serrated proximal edge 19 to aid in engaging an item.

The pull rod 14 has a proximal portion 21 and a distal end 22 connected to the engagement head 13. The pull rod 14 is movable within the catheter 12 to selectively extend and retract the engagement head 13 from the distal end 16 of the catheter 12. The pull rod 14 is spaced radially inwardly from said serrated proximal edge 19 so that the pull rod 14 does not interfere with an item being placed between the distal end 16 of the catheter and the serrated proximal edge 19 of the engagement head 13 in any rotated orientation of the catheter 12. For example, the pull rod 14 can be concentric with the serrated proximal edge 19 and attached to the engagement head 13 within the internal relief area 20, as illustrated.

An interior guide 23 is attached to an interior surface of the catheter 12 near the distal end 16 of the catheter 12 to keep the pull rod 14 centered within the catheter 12 as the engagement head 13 is extended and retracted. The interior guide 23 is rigid to provide positive engagement of the pull rod 14 while allowing a remainder of the catheter 12 to be flexible. The pull rod 14 has a distal portion 24 that is more rigid than the proximal portion 21 of the pull rod 14 to allow positive orientation of the engagement head 13 to be maintained relative to the distal end 16 of the catheter 12 while allowing the proximal portion 21 of the pull rod 14 to be flexible.

Figure 3:
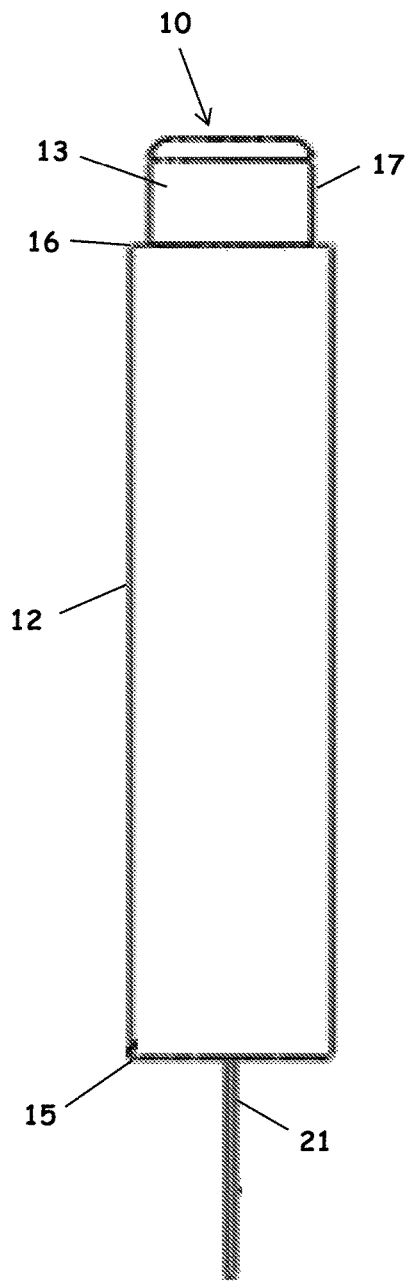
FIG. 3 is an elevation view of a removal assist device of the present invention, with an engagement head in a retracted position.
Figure 4:
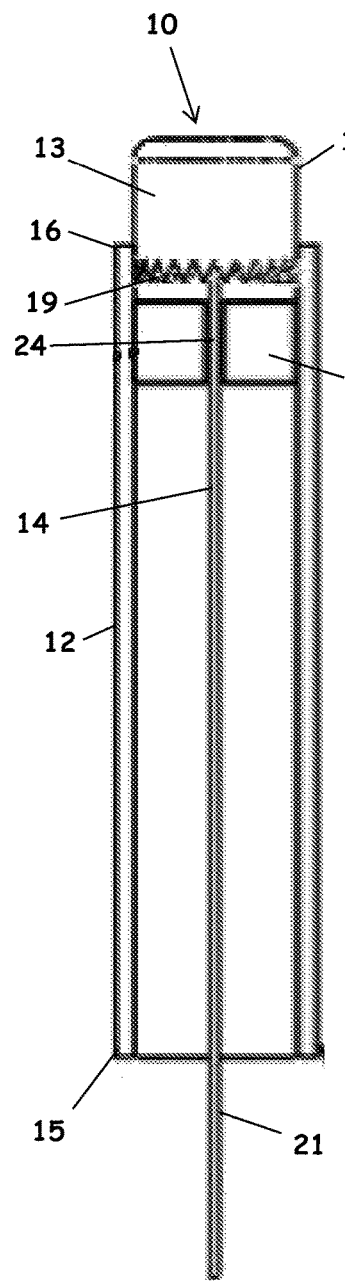
FIG. 4 is a cross sectional view of the removal assist device with the engagement head in a retracted position.
Figure 5:
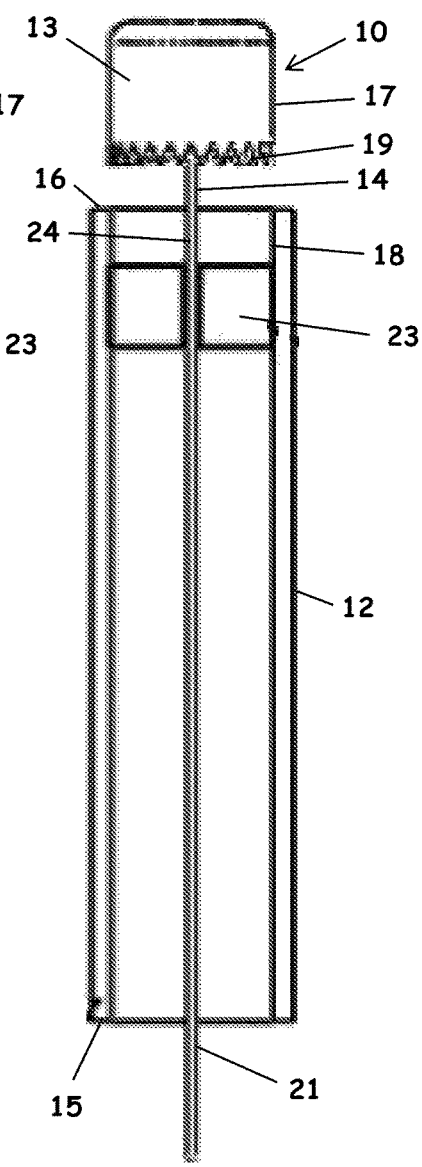
FIG. 5 is a cross sectional view of the removal assist device with the engagement head in an extended position.

In FIGS. 3 and 4, the catheter 12 is shown with the engagement head 13 in its retracted position. The catheter 12 can be inserted into a vein with the engagement head 13 retracted, and then extended, as shown in FIG. 5, by advancing the pull rod 14. The interior guide 23 is attached to the interior of the catheter 12 and serves to keep proper orientation of the pull rod 14 as the engagement head 13 is advanced and retracted. The interior guide 23 can be fairly rigid, allowing positive encasement of the pull rod 14 while allowing the remainder of the catheter 12 to be flexible. The pull rod 14 can also be rigid at its distal portion 24 allowing positive orientation to be maintained, while the proximal portion 21 of the pull rod 14 can be flexible.

Figure 6:
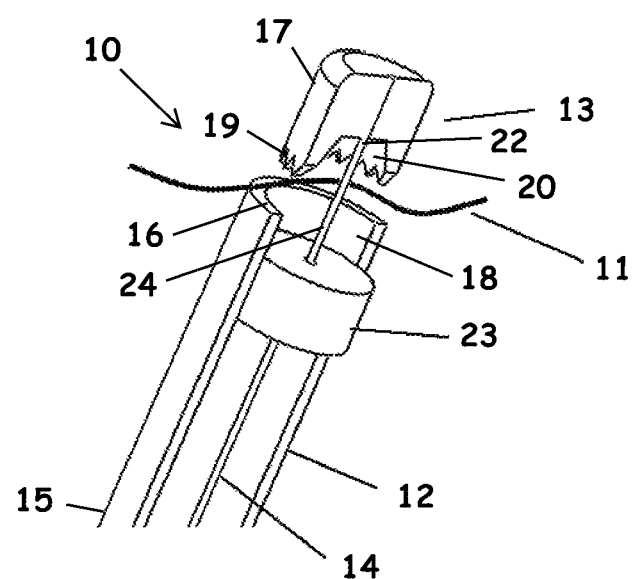
FIG. 6 is a perspective cutaway view of the removal assist device with the engagement head in an extended position and a filter strut positioned to be grabbed by the engagement head.

Once inserted, the catheter 12 can then be moved through torquing, rotating the dual lumen retrieval catheter, and/or advancing or retracting the catheter until the IVC filter or strut 11 of the filter is engaged, as shown in FIG. 6. Once engaged, the pull rod 14 is retracted to close the engagement head 13 onto the IVC filter strut 11. The entire catheter 12 can then be advanced/retracted/torqued to dislodge the IVC filter from the vein wall.

While the invention has been specifically described in connection with a specific embodiment thereof, it is to be understood that this is by way of illustration and not of limitation, and the scope of the appended claims should be construed as broadly as the prior art will permit.

What is claimed is:

1. A device for assisting in the removal of items endovascularly, comprising:
    a catheter having a proximal end and a distal end;
    an engagement head arranged to be extended from and retracted into the catheter; and
    a pull rod having a proximal portion and a distal end connected to the engagement head, said pull rod being movable within the catheter to selectively extend and retract the engagement head from the distal end of the catheter;
    wherein said engagement head comprises a generally cylindrical outer shape that corresponds in shape and size to an internal surface of the catheter;
    wherein said engagement head comprises a serrated proximal edge arranged to extend beyond the distal end of the catheter when said engagement head is extended from the catheter and to grab and hold an item between the serrated proximal edge and the distal end of the catheter as the engagement head is being retracted into the catheter; and
    wherein said serrated proximal edge of said engagement head is generally circular.

2. The device according to claim 1, wherein said engagement head has an internal relief area located radially inwardly from said serrated proximal edge to aid in engaging an item.

3. The device according to claim 2, wherein said pull rod is concentric with said serrated proximal edge and attached to said engagement head within said internal relief area.

4. The device according to claim 1, further comprising an interior guide attached to an interior of the catheter near a distal end of the catheter to keep the pull rod centered within the catheter as the engagement head is extended and retracted.

5. The device according to claim 4, wherein said interior guide is rigid to provide positive engagement of the pull rod while allowing a remainder of the catheter to be flexible.

6. A device for assisting in the removal of items endovascularly, comprising:
- a catheter having a proximal end and a distal end;
- an engagement head arranged to be extended from and retracted into the catheter; and
- a pull rod having a proximal portion and a distal end connected to the engagement head, said pull rod being movable within the catheter to selectively extend and retract the engagement head from the distal end of the catheter;
- further comprising an interior guide attached to an interior of the catheter near a distal end of the catheter to keep the pull rod centered within the catheter as the engagement head is extended and retracted;
- wherein said interior guide is rigid to provide positive engagement of the pull rod while allowing a remainder of the catheter to be flexible; and
- wherein the pull rod has a distal portion that is more rigid than the proximal portion of the pull rod to allow positive orientation of the engagement head to be maintained relative to the distal end of the catheter while allowing the proximal portion of the pull rod to be flexible.

7. A device for assisting in the removal of items endovascularly, comprising:
- a catheter having a proximal end and a distal end;
- an engagement head that can be extended from and retracted into the catheter, said engagement head comprising a cylindrical outer shape that corresponds to an internal surface of the catheter, and a serrated proximal edge that is generally circular and faces in a proximal direction, said serrated proximal edge being arranged to extend beyond the distal end of the catheter when said engagement head is extended from the catheter and to grab and hold an item between the proximal edge and the distal end of the catheter as the engagement head is being retracted into the catheter; and
- a pull rod having a proximal portion and a distal end connected to the engagement head, said distal end of said pull rod being spaced radially inwardly from said proximal edge, and said pull rod being movable within the catheter to selectively extend and retract the engagement head from the distal end of the catheter.

8. The device according to claim 7, wherein said engagement head has an internal relief area located radially inwardly from said proximal edge to aid in engaging an item.

9. The device according to claim 8, wherein said pull rod is concentric with said proximal edge.

10. The device according to claim 7, further comprising an interior guide attached to an interior of the catheter near a distal end of the catheter to keep the pull rod centered within the catheter as the engagement head is extended and retracted.

11. The device according to claim 10, wherein said interior guide is rigid to provide positive engagement of the pull rod while allowing a remainder of the catheter to be flexible.

12. A device for assisting in the removal of items endovascularly, comprising:
- a catheter having a proximal end and a distal end;
- an engagement head that can be extended from and retracted into the catheter, said engagement head comprising a cylindrical outer shape that corresponds to an internal surface of the catheter, and a proximal edge that is generally circular and faces in a proximal direction, said engagement head being arranged to grab and hold an item between the proximal edge and the distal end of the catheter; and
- a pull rod having a proximal portion and a distal end connected to the engagement head, said distal end of said pull rod being spaced radially inwardly from said proximal edge, and said pull rod being movable within the catheter to selectively extend and retract the engagement head from the distal end of the catheter;
- further comprising an interior guide attached to an interior of the catheter near a distal end of the catheter to keep the pull rod centered within the catheter as the engagement head is extended and retracted;
- wherein said interior guide is rigid to provide positive engagement of the pull rod while allowing a remainder of the catheter to be flexible; and
- wherein the pull rod has a distal portion that is more rigid than the proximal portion of the pull rod to allow positive orientation of the engagement head to be maintained relative to the distal end of the catheter while allowing the proximal portion of the pull rod to be flexible.

* * * * *